United States Patent [19]

Aberg

[11] Patent Number: 6,123,961
[45] Date of Patent: *Sep. 26, 2000

[54] TREATING URINARY INCONTINENCE WITH (R)-DESETHYLOXYBUTYNIN AND (R)-OXYBUTYNIN

[75] Inventor: A. K. Gunnar Aberg, Sarasota, Fla.

[73] Assignee: Bridge Pharma, Inc., Sarasota, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/936,782

[22] Filed: Sep. 23, 1997

Related U.S. Application Data

[60] Provisional application No. 60/026,672, Sep. 25, 1996, abandoned.

[51] Int. Cl.[7] .............................. A61K 33/24; A61K 9/20; A61K 9/14; A61K 9/48
[52] U.S. Cl. .................... 424/468; 424/436; 424/451; 424/449; 424/464; 424/489; 514/617; 514/964; 514/966; 514/962
[58] Field of Search ..................................... 424/464, 449, 424/451, 468, 436, 489; 514/617, 310, 946, 966, 964, 962

[56] References Cited

U.S. PATENT DOCUMENTS 5,532,278  7/1996  Aberg et al. .
5,677,346  10/1997  Aberg et al. .
5,736,577  4/1998  Aberg et al. .

OTHER PUBLICATIONS

The Journal of Pharmacology and Experimental Therapeutics vol. 256, No. 2; 1990; pp 562–567.

The Journal of Pharmacology and Experimental Therapeutics vol. 247, No. 3; 1988; pp. 867–872.

Human and Experimental Toxicology (1991), 10, pp. 225–226.

American Urological Association, Inc. 1997 Annual Meeting publication; Topic No. 17; Apr. 12–17, 1997.

Noronha–Blob et al, "Enantiomers of Oxybutynin: In Vitro Pharmacological Characterization . . . " J. Pharmacol. Exp. Ther. 256 (2), 562–567, 1990.

*Primary Examiner*—Thurman K. Page
*Assistant Examiner*—Brian K. Seidleck
*Attorney, Agent, or Firm*—Nields, Lemack & Dingman

[57] ABSTRACT

A method for treating or preventing urinary incontinence and other motility disorders involving the urethrogenital tract, by administering to a mammal an effective amount of the R-isomers of 4-diethylamino-2-butynyl cyclohexylphenylglycolate and 4-ethylamino-2-butynyl cyclohexylphenylglycolate and pharmaceutically acceptable salts thereof.

12 Claims, No Drawings

TREATING URINARY INCONTINENCE WITH (R)-DESETHYLOXYBUTYNIN AND (R)-OXYBUTYNIN

This application claims the benefits of U.S. Provisional Application No. 60/026,672, filed Sep. 25, 1996, now abandoned.

FIELD OF THE INVENTION

The invention relates to a the optically active R(−)-isomer of 4-diethylamino-2-butynyl cyclohexylphenylglycolate and to the optically active metabolite thereof, called R(−)-4-ethylamino-2-butynyl cyclohexylphenylglycolate. The compound 4-diethylamino-2-butynyl cyclohexylphenylglycolate has the generic name oxybutynin (OXY) and is an approved drug for the management of urinary incontinence.

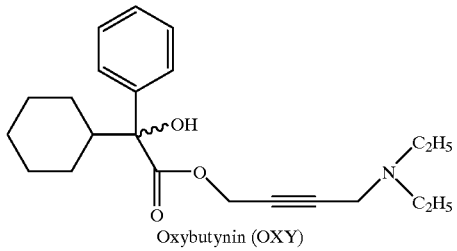

Oxybutynin (OXY)

The compound 4-ethylamino-2-butynyl cyclohexylphenylglycolate is called desethyloxybutynin (DEO) and has the following chemical structure:

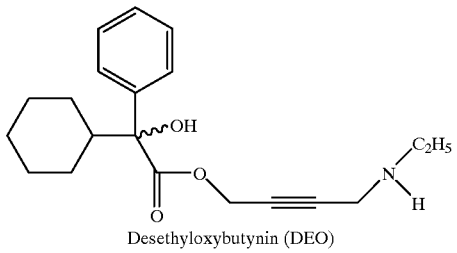

Desethyloxybutynin (DEO)

BACKGROUND OF THE INVENTION

Racemic oxybutynin (OXY) is used therapeutically in the treatment of urinary incontinence due to detrusor muscle instability. OXY exerts a spasmolytic effect by inhibiting the receptors for acetylcholine on smooth muscle. OXY is selective for muscarinic acetylcholine receptors over nicotinic receptors and as a result, no blocking effects are observed at skeletal neuromuscular junctions.

In patients with conditions characterized by involuntary bladder contractions, clinical studies have demonstrated that OXY increases bladder capacity, diminishes the frequency of involuntary contractions of the detrusor muscle, and delays the initial desire to void. OXY is therefore useful in the treatment and prevention of both incontinency and frequent voluntary urination. Antimuscarinic side effects of OXY, such as mydriasis, xerostomia and tachycardia, cannot be avoided with this drug since therapeutic anticholinergic effects are sought [Lish et al. Arch. Int. Pharmacodyn. 156, 467–488 (1965), 481].

Racemic oxybutynin consists of a 50/50 mixture of R(−)-oxybutynin and S(+)-oxybutynin. It has been shown that practically all of the anticholinergic activity of OXY resides in the R(−)-isomer, and the S(+)-isomer carries only a small fraction of the drug's anticholinergic activity (Noronha-Blob et al., J. Pharmacol. Exp. Ther., 1991, 256: 562–567). However, it has now been shown that more serious toxicological activities of oxybutynin express cardiovascular depression and possibly also respiratory depression.

One clinically important metabolite of OXY has been identified in humans after administration of OXY and is called desethyloxybutynin (DEO) (Westlin, L., 1985. Internal report, Smith & Nephew Pharmaceuticals Ltd.). A second metabolite, called N-oxide-oxybutynin, has been suggested but may not be chemically stable (Lindeke B. et al., 1981 Metabolism of Oxybutynin . . . Biomed Mass Spectrometry. 1981, 8:506–513).

SUMMARY OF THE INVENTION

It has now unexpectedly been found that the S(+)-isomers of oxybutynin and of desethyloxybutynin carry most of the serious cardiovascular depressing activity of oxybutynin. This unwanted side effect is of concern in all patients given racemic oxybutynin and particularly in patients that are of age or patients that have pre-existing cardiovascular conditions. It was found that the R(−)-isomer of oxybutynin quite unexpectedly was much better tolerated than the S(+)-isomer, when given to laboratory animals. It has furthermore now been found that the R(−)-isomers of oxybutynin and of desethyloxybutynin provide superior therapeutic effects when compared to their corresponding racemates and their optical antipodes. Thus, the active compounds of the present invention are the R(−)-isomer of oxybutynin and the R(−)-isomer of desethyloxybutynin.

CHEMISTRY

Racemic oxybutynin is 4-diethylamino-2-butynyl α-cyclohexyl-α-hydroxybenzeneacetate, also known as 4-diethylamino-2-butynyl cyclohexylphenylglycolate and herein also referred to as OXY. The generic name given to to the hydrochloride salt of racemic oxybutynin by the USAN Council is oxybutynin chloride; it is sold under the name of Ditropan®.

R(−)-oxybutynin is R(−)-and herein also referred to as R-OXY. No generic name is known for this compound or any of its salts.

Racemic desethyloxybutynin is 4-ethylamino-2-butynyl cyclohexylphenylglycolate and is a known metabolite of oxybutynin (Hughes K. M. et al. Measurement of oxybutynin and its N-desethyl metabolite in plasma . . . Xenobiotica, 1992, 7: 859–869). This compound is herein also referred to as DEO. No generic name is known for this compound or any of its salts.

R(−)-desethyloxybutynin is R(−)-4-ethylamino-2-butynyl cyclohexylphenylglycolate and herein also referred to as R-DEO. No generic name is known for this compound or any of its salts.

The overall process for preparing R-OXY involves:
(a) the preparation of 4-diethylamino-2-butynyl chloride from dichlorobutyne
(b) by standard esterification technique, reacting the single R-enantiomer of cyclohexylphenylglycolic acid with the prepared 4-diethylamino-2-butynyl chloride to the R-enantiomer of 4-diethylamino-2-butynyl cyclohexylphenylglycolate.

The process for preparing R-DEO involves:
(a) the preparation of the side chain 4-ethylamino-2-butynyl chloride from dichlorobutyne (b) by standard esterification technique, reacting the R-enantiomer of cyclohexylphenylglycolic acid with the selected side chain to produce the R(−)-enantiomer of 4-ethylamino-2-butynyl cyclohexylphenylglycolate.

Alternative processes for preparing the compounds of the invention involve the preparation of hydroxylated side chains instead of the above mentioned halogenated side chains.

Racemic cyclohexylphenylglycolic acid is commercially available from SIPSY Chem Corp., 2137 Route 33, Suite 2, Hamilton Square, N.J. 08690.

The R-enantiomer of cyclohexylphenylglycolic acid can be obtained by resolvation of racemic cyclohexylphenylglycolic acid.

R-OXY and R-DEO can also be prepared by the resolution of racemic material, using conventional means such as fractional crystallization of diastereomeric salts with chiral acids. Other standard methods of resolution known to those skilled in the art, include, but are not limited to, simple crystallization and chromatography on a chiral substrate, and can also be used.

DOSING, DOSAGE FORMS, PHARMACEUTICAL COMPOSITIONS

The magnitude of a prophylactic or therapeutic dose of the compounds of this invention in the acute or chronic management of disease will vary with the severity and nature of the condition to be treated and the route of administration. The dose and the frequency of the dosing will also vary according to the age, body weight and response of the individual patient. In general, the total daily dose range for the compounds of this invention for the conditions described herein is from about 1 mg to about 100 mg in single or divided doses, preferably in divided doses. In managing the patient, the therapy should be initiated at a lower dose, perhaps at about 0.5 mg to about 25 mg, and may be increased up to about 200 mg depending on the patient's global response. It is further recommended that patients over 65 years and those with impaired renal or hepatic function initially receive low doses and that they be titrated based on individual response(s) and plasma drug level(s). It may be necessary to use dosages outside these ranges, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat urinary incontinence but insufficient to cause adverse effects" are encompassed by the above-described dosage amounts and dose frequency schedule.

Any suitable route of administration may be employed for providing the patient with an effective dosage of the compounds of this invention. For example, oral, sublingual, rectal, parental (subcutaneous, intramuscular, intravenous), intraocular, transdermal, aerosol and like forms of administration may be employed. Dosage forms include tablets, troches, dispersions, suspensions, solutions, capsules, microencapsulated systems, sprays, transdermal delivery systems, and the like.

The pharmaceutical compositions of the present invention comprise a compound of the present invention as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzene-sulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, succinic, sulfuric, tartaric, p-toluenesulfonic, and the like. The hydrochloride is particularly preferred.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent one of the more advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos. 3,845,770; 3,916,899; 3,536,809; 3,598,123; and 4,008,719, and PCT application WO92/20377, the disclosures of which are hereby incorporated by reference.

Pharmaceutical compositions of the present invention suitable for oral administration may be presented as discrete unit dosage forms such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for the racemic mixture.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet may contain from about 0.5 mg to about 25 mg of the active ingredient.

EXAMPLES

Example 1

ORAL UNIT DOSAGE FORMULATION
Tablets:

| Ingredients | per tablet | per batch of 10,000 tablets |
|---|---|---|
| R-OXY or R-DEO | 5 mg | 50 g |
| Microcrystalline cellulose | 30 mg | 300 g |

-continued

ORAL UNIT DOSAGE FORMULATION
Tablets:

| Ingredients | per tablet | per batch of 10,000 tablets |
|---|---|---|
| Lactose | 70 mg | 700 g |
| Calcium stearate | 2 mg | 20 g |
| FD&C Blue #1 Lake | 0.03 mg | 300 mg |

The selected compound of the present invention is blended with the lactose and cellulose until a uniform blend is formed. The lake is added and further blended. Finally, the calcium stearate is blended in, and the resulting mixture is compressed into tablets using a 9/32 inch (7 mm) shallow concave punch. Tablets of other strengths may be prepared by altering the ration of active ingredient to the excipients or to the final weight of the tablet.

The surprising utility of the compounds of the present invention have been established by the following studies.

Example 2

Pharmacological Studies
MATERIALS AND METHODS
 1. Acute Toxicity in Mice.

The experiments are carried out on conscious albino mice that are administered intravenously or orally escalating doses of the test compounds.

2. Ligand Binding Studies: Muscarinic Receptors.

The experiments are carried out on membranes prepared from SF9 cells infected with baculovirus to express human recombinant muscarinic receptor subtypes. After incubation with the test article and the proper radioligand and washing, bound radioactivity is determined with a liquid scintillation counter, using a commercial scintillation cocktail. The specific radioligand binding to each receptor is defined as the difference between total binding and nonspecific binding determined in the presence of an excess of unlabelled ligand. $IC_{50}$ values (concentrations required to inhibit 50% of specific binding) are determined by non linear regression analysis of the competition curves. These parameters are obtained by curve fitting using Sigmaplot™ software.

3. Cardic Depression Studies.

Spontaneously beating isolated cardiac tissues, are superfused or submerged in an oxygenated physiological solution of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7., or a similar balanced physiological solution. They are maintained at 37.5 C. Contractions and frequency of contractions are recorded with transducers on an ink-writing polygraph. In each experiment up to six isolated cardiac tissue samples are studied at each doselevel, suspended in individual tissue chambers and allowed to equilibrate with the bathing solution before proceeding with the experiment. The results obtained are expressed in percent change and evaluated statistically, using standard methodology.

4. Functional Characterization of Antimuscarinic/Antispasmodic Activity.

Strips of intestinal smooth muscle tissue are removed from the body of male Hartley guinea pigs weighing 400–600 g. The strips are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7, or a similar balanced physiological solution. They are maintained at constant temperature. Contractions are recorded with isometric transducers (Model FT-10) on an ink-writing polygraph. In each experiment up to seven strips are removed from a single animal, suspended in individual tissue chambers and allowed to equilibrate with the bathing solution for one hour before proceeding with the experiment. In order to assess the viability of each tissue and to serve as a frame of reference, contractions of each strip of tissue are recorded initially in response to exposure to a tissue medium in which the NaCl was replaced by KCl to yield a concentration of 137.7 mM KCl in the medium. This is followed by return to the standard medium, and then by exposures to progressively creasing concentrations of carbachol, with separate exposures to each concentration only until the peak response has been recorded. Then, leaving one strip untreated and/or one strip exposed to the test solution to serve as control tissue(s), the remaining strips each are exposed for one hour to one concentration of an antagonist. Finally, the responses to increasing concentrations of carbachol followed by exposure to 137.7 mM KCl are recorded a second time. To determine whether antagonists decrease the peak response to agonists, the peak tension developed by each strip during the second set of determinations is expressed as a percent of the peak tension developed during the first concentration-effect determination. Then, for each antagonist the resultant data are analyzed using standard statistical methodology.

What is claimed is:

1. A method for treating urinary incontinence while reducing concomitant liability of adverse effects associated with racemic oxybutynin, which comprises administering to a human in need of such treatment a therapeutically effective amount of R(−)-4-diethylamino-2-butynyl cyclohexylphenylglycolate or a pharmaceutically acceptable salt thereof, substantially free of its corresponding S-enantiomer.

2. A method for treating urinary incontinence while reducing concomitant liability of adverse effects associated with racemic oxybutynin, which comprises administering to a human in need of such treatment a therapeutically effective amount of R(−)-4-ethylamino-2-butynylcyclohexylphenylglycolate or a pharmaceutically acceptable salt thereof, substantially free of its corresponding S-enantiomer.

3. The method of claim 1 wherein R(−)-4-diethylamino-2-butynyl cyclohexylphenylglycolate or a pharmaceutically acceptable salt thereof is administered by inhalation or by parenteral, transdermal, rectal, sublingual or oral administration.

4. The method of claim 2 wherein R(−)-4-ethylamino-2-butynyl cyclohexylphenylglycolate or a pharmaceutically acceptable salt thereof is administered by inhalation or by parenteral, transdermal, rectal, sublingual or oral administration.

5. The method of claim 1 wherein R(−)-4-diethylamino-2-butynyl cyclohexylphenylglycolate or a pharmaceutically acceptable salt thereof is administered by oral administration.

6. The method of claim 2 wherein R(−)-4-ethylamino-2-butynyl cyclohexylphenylglycolate or a pharmaceutically acceptable salt thereof is administered by oral administration.

7. The method of claim 1 wherein R(−)-4-diethylamino-2-butynyl cyclohexylphenylglycolate or a pharmaceutically acceptable salt thereof is administered orally in an extended release formulation.

8. The method of claim 2 wherein R(−)-4-ethylamino-2-butynyl cyclohexylphenylglycolate or a pharmaceutically acceptable salt thereof is administered orally in an extended release formulation.

9. The method of claim 1 wherein R(−)-4-diethylamino-2-butynyl cyclohexylphenylglycolate or a pharmaceutically acceptable salt thereof is administered transdermally.

10. The method of claim 2 wherein R(−)-4-ethylamino-2-butynyl cyclohexylphenylglycolate or a pharmaceutically acceptable salt thereof is administered transdermally.

11. The method of claim 1 wherein R(−)-4-diethylamino-2-butynyl cyclohexylphenylglycolate or a pharmaceutically acceptable salt thereof is administered from about 1 mg to about 200 mg per day.

12. The method of claim 2 wherein R(−)-4-ethylamino-2-butynyl cyclohexylphenylglycolate or a pharmaceutically acceptable salt thereof is administered from about 1 mg to about 200 mg per day.

* * * * *